(12) United States Patent
Hampton et al.

(10) Patent No.: US 8,313,066 B2
(45) Date of Patent: Nov. 20, 2012

(54) INTRAVENOUS FLUID CONTAINER STAND AND METHODS FOR MAKING SAME

(75) Inventors: Linda M. Hampton, Bristol, WI (US); Ishwor Prasad Adhikari, Mundelein, IL (US)

(73) Assignee: Medline Industries, Inc., Mundelein, IL (US)

( * ) Notice: Subject to any disclaimer, the term of this patent is extended or adjusted under 35 U.S.C. 154(b) by 802 days.

(21) Appl. No.: 12/146,147

(22) Filed: Jun. 25, 2008

(65) Prior Publication Data
US 2009/0321589 A1    Dec. 31, 2009

(51) Int. Cl.
*F16L 3/00* (2006.01)
(52) U.S. Cl. ............... 248/121; 248/158; 248/125.8; 16/30; 16/43; 16/31 R; 411/348
(58) Field of Classification Search ............ 16/30, 43, 16/31 R; 248/121, 128, 158; 411/348
See application file for complete search history.

(56) References Cited

U.S. PATENT DOCUMENTS

| | | | | |
|---|---|---|---|---|
| 2,313,883 A | * | 3/1943 | Lowther | 269/48.4 |
| 2,350,630 A | * | 6/1944 | Melcher | 269/48.4 |
| 2,373,083 A | * | 4/1945 | Brewster | 411/348 |
| 2,393,587 A | * | 1/1946 | Bugg et al. | 269/48.4 |
| 2,902,592 A | | 9/1959 | Cole et al. | 362/277 |
| 2,957,187 A | | 10/1960 | Raia | |
| 3,117,484 A | * | 1/1964 | Myers | 411/348 |
| 3,183,586 A | * | 5/1965 | Sellers | 29/441.1 |
| 3,486,185 A | * | 12/1969 | Lange | 16/18 R |
| 3,596,554 A | * | 8/1971 | Low et al. | 411/348 |
| 3,709,556 A | | 1/1973 | Allard et al. | |
| 3,752,493 A | | 8/1973 | McWhorter | |
| 4,190,224 A | | 2/1980 | LeBlanc et al. | |
| D264,379 S | | 5/1982 | Slinkard | |
| 4,392,690 A | | 7/1983 | Anderson | |
| 4,477,121 A | | 10/1984 | Atkins | |
| 4,511,157 A | | 4/1985 | Wilt, Jr. | |
| 4,511,158 A | | 4/1985 | Varga et al. | |
| 4,541,596 A | | 9/1985 | Price | |
| 4,572,536 A | | 2/1986 | Doughty | |
| 4,582,448 A | | 4/1986 | Costello et al. | |

(Continued)

FOREIGN PATENT DOCUMENTS

WO    WO 87/02754    5/1987

(Continued)

OTHER PUBLICATIONS

*Darcor* "Innovators in Motion Technology Catalogue 2000", pp. 45-47, electronically available at http://www.darcor.com/public/File/pdf/Darcor_Casters_Product_Catalogue.PDF (last visited Sep. 19, 2008).

(Continued)

*Primary Examiner* — Terrell McKinnon
*Assistant Examiner* — Daniel J Breslin
(74) *Attorney, Agent, or Firm* — Nixon Peabody LLP

(57) ABSTRACT

According to one embodiment, an intravenous stand for supporting an intravenous fluid container includes a hanger configured to support one or more intravenous fluid containers. A pole, having a first end and a second end, is coupled to the hanger at the first end and a base at the second. A plurality of casters are releasably coupled to the base via a plurality of quick-release members.

9 Claims, 11 Drawing Sheets

U.S. PATENT DOCUMENTS

| | | |
|---|---|---|
| 4,666,111 A | 5/1987 | Schuler |
| 4,681,495 A * | 7/1987 | Crespin et al. ................. 411/298 |
| 4,719,663 A | 1/1988 | Termini |
| 4,725,027 A | 2/1988 | Bekanich |
| 4,788,741 A * | 12/1988 | Hilborn ......................... 16/35 R |
| 4,805,941 A | 2/1989 | Downing et al. |
| 4,832,294 A | 5/1989 | Eidem |
| 4,901,980 A | 2/1990 | Hansen |
| 4,966,340 A | 10/1990 | Hunter |
| 4,969,768 A | 11/1990 | Young |
| 5,083,807 A | 1/1992 | Bobb et al. |
| 5,094,418 A | 3/1992 | McBarnes, Jr. et al. |
| 5,112,019 A | 5/1992 | Metzler et al. |
| 5,135,191 A | 8/1992 | Schmuhl |
| 5,149,036 A | 9/1992 | Sheehan |
| 5,219,139 A | 6/1993 | Hertzler et al. |
| 5,230,496 A | 7/1993 | Shillington et al. |
| 5,236,213 A | 8/1993 | Trickett |
| 5,344,169 A | 9/1994 | Pryor et al. |
| 5,347,681 A | 9/1994 | Wattron et al. |
| 5,355,539 A | 10/1994 | Boettger |
| 5,358,205 A | 10/1994 | Starkey et al. |
| 5,374,074 A | 12/1994 | Smith |
| 5,458,305 A | 10/1995 | Woodward |
| 5,476,275 A | 12/1995 | Baechler et al. |
| 5,551,105 A | 9/1996 | Short |
| 5,594,974 A | 1/1997 | Wattron et al. |
| 5,699,988 A | 12/1997 | Boettger et al. |
| 5,704,577 A | 1/1998 | Gordon |
| 5,727,850 A * | 3/1998 | Masclet ................... 301/111.03 |
| 5,740,584 A | 4/1998 | Hodge et al. |
| 5,742,977 A * | 4/1998 | Hoofe, III ........................ 16/30 |
| 5,772,162 A | 6/1998 | Lin ................................. 248/121 |
| 5,776,105 A | 7/1998 | Corn |
| 5,820,086 A | 10/1998 | Hoftman et al. ........... 248/125.2 |
| 5,857,685 A | 1/1999 | Phillips et al. |
| 5,924,658 A | 7/1999 | Shiery et al. |
| 6,079,678 A | 6/2000 | Schott et al. |
| 6,182,662 B1 | 2/2001 | McGhee |
| 6,193,323 B1 | 2/2001 | Lin |
| 6,253,891 B1 | 7/2001 | Miller |
| 6,267,452 B1 | 7/2001 | Lin |
| 6,279,926 B1 | 8/2001 | Taube et al. |
| 6,375,133 B1 | 4/2002 | Morrow |
| 6,386,789 B1 * | 5/2002 | Chausse et al. ............. 403/322.2 |
| 6,390,311 B1 | 5/2002 | Belokin ......................... 211/204 |
| 6,619,599 B2 | 9/2003 | Elliott et al. |
| 6,634,665 B2 | 10/2003 | Hargroder |
| 6,708,991 B1 | 3/2004 | Ortlieb |
| 6,722,711 B2 * | 4/2004 | Kitzis ............................ 292/145 |
| 6,796,001 B1 * | 9/2004 | Finkelstein ....................... 16/32 |
| 6,810,561 B1 * | 11/2004 | Liu ................................ 16/42 T |
| 6,969,031 B2 | 11/2005 | Ugent et al. |
| 7,011,321 B2 | 3/2006 | Hargroder |
| 7,207,532 B1 | 4/2007 | Roberts et al. |
| 7,281,691 B2 | 10/2007 | Adelman |
| 7,314,200 B2 | 1/2008 | Bally et al. |
| 7,431,531 B2 * | 10/2008 | Carnevali ....................... 403/328 |
| 7,552,508 B2 * | 6/2009 | Underwood .................. 16/31 R |
| 7,594,874 B2 * | 9/2009 | Meissner ......................... 482/36 |
| 7,731,465 B2 * | 6/2010 | Stapulionis et al. .......... 411/348 |
| 2002/0038843 A1 | 4/2002 | Footitt et al. ................ 248/188.7 |
| 2002/0096608 A1 | 7/2002 | Cedarberg, III |
| 2002/0104934 A1 | 8/2002 | Elliott et al. |
| 2005/0116126 A1 | 6/2005 | Ugent et al. |
| 2007/0023587 A1 | 2/2007 | Eggleston et al. |
| 2007/0176063 A1 | 8/2007 | Heimbrock et al. |
| 2007/0221796 A1 | 9/2007 | Silverman et al. |
| 2007/0267550 A1 | 11/2007 | Blankenship et al. |
| 2007/0267551 A1 | 11/2007 | Townsend |
| 2008/0011907 A1 | 1/2008 | Jacobsma |
| 2008/0054132 A1 | 3/2008 | Muncie |

FOREIGN PATENT DOCUMENTS

| | | |
|---|---|---|
| WO | WO 02/09632 | 2/2002 |

OTHER PUBLICATIONS

Partial European Search Report corresponding to co-pending European Patent Application Serial No. 09163755.3, European Patent Office, Oct. 26, 2009; 5 pages.

Extended European Search Report corresponding to co-pending European Patent Application Serial No. 09163755.3, European Patent Office, Feb. 18, 2010; 11 pages.

* cited by examiner

INTRAVENOUS FLUID CONTAINER STAND AND METHODS FOR MAKING SAME

FIELD OF THE INVENTION

The present invention relates generally to intravenous container stands and, in particular, to transportable intravenous container stands having releasably coupled casters.

BACKGROUND

For many years, patients receiving intravenous ("IV") fluid transfusions have been able to remain ambulatory during such transfusions by using mobile IV stands. While walking or moving in a wheelchair, the patient rolls the IV stand alongside him or her within reach of tubings through which intravenous fluids flow from one or more medication containers. However, as explained in more detail below, conventional IV stands have many problems.

Typically, conventional IV stands have casters or wheels that are permanently fixed to a pole base via nuts and bolts. The casters often become defective due to normal wear-and-tear, misuse, accidents, or other factors. For example, contaminants (such as dirt or dust) can accumulate on rotational components of the casters, interfering with the proper multi-directional movement of the IV stand. As a result, the casters lose mobility and tend to be oriented in opposing directions such that the IV stand becomes difficult to control. Often, only a single caster requires replacement to correct this problem. To replace the caster, the IV stand is typically sent to a separate maintenance department, where a designated maintenance worker uses appropriate tools to replace the caster.

The typical procedure for replacing a defective caster presents several problems that are caused by the permanent attachment of the caster to the pole base. One problem is that it is sometimes not feasible to remove the IV stand while it is coupled to a patient. Thus, the replacement of a defective caster must be delayed until the IV stand is no longer required by the patient, or until an appropriate replacement is located.

The delay in replacing the defective caster can have potentially disastrous consequences. For example, if the patient attempts to move, the IV stand can tip over and cause severe injury to the patient by pulling out catheters inserted in the patient's body and coupled to IV containers (e.g., medication bags) supported by the IV stand. Similarly, a falling IV stand can cause damage and/or injury to other nearby objects and people.

Although the defective IV stand can be replaced with a properly functioning IV stand, this presents additional problems. For example, replacing the IV stand presents the risk that an IV bag may be dropped and, potentially, break. In some cases, there can be multiple IV tubes from multiple IV bags connected to a patient. Further complicating IV stand replacement, other equipment such as pumps and monitors are often attached to the IV stand and need to be turned on and off to be properly transferred from one IV stand to another.

The increased labor requirements for repairing broken casters and/or transferring IV bags and equipment from one IV stand to another IV stand greatly increases medical costs. In addition, valuable hospital space is wasted to store more IV stands than are truly necessary, and patient safety is potentially risked every time IV bags are transferred from a defective IV stand to another IV stand.

Another problem associated with conventional IV stands is that they typically include multiple pole sections that can rotate relative to one another. As a result, the tubes extending from the IV containers to the patient can become entangled or wrapped around the pole, reducing the slack of the tubes between the patient and the IV stand. Eventually, the tubes can pull on the patient causing discomfort or pain where the IV is inserted into the patient. Worse still, the tubes may be accidentally and painfully removed from the patient.

Thus, a need exists for an IV stand with casters that can be quickly replaced, without the use of tools. Another need exists to prevent the relative rotation between pole sections of an IV stand.

SUMMARY

According to one embodiment, an intravenous stand for supporting an intravenous fluid container includes a hanger configured to support one or more intravenous fluid containers. A pole, having a first end and a second end, is coupled to the hanger at the first end and a base at the second. A plurality of casters are releasably coupled to the base via a plurality of quick-release members.

According to another embodiment, an intravenous stand for supporting an intravenous fluid container includes a hanger configured to support one or more intravenous fluid containers and an upper pole, having a first end and a second end, coupled to the hanger at the first end of the upper pole. The intravenous stand further includes a lower pole having a first end and a second end. The second end of the upper pole is coupled to the first end of the lower pole by an insert. The insert has a shape that is configured to prevent rotational movement between the upper pole and the lower pole. A base is coupled to the second end of the lower pole and a plurality of casters are releasably coupled to the base.

In yet another embodiment, a method of making an intravenous stand for supporting an intravenous fluid container with quickly releasable casters includes providing a hanger that is configured to support one or more intravenous fluid containers and coupling a pole to the hanger at a first end of the pole. The method of making an intravenous stand further includes coupling a base to the pole at a second end of the pole and releasably coupling a plurality of casters to the base via a plurality of quick-release members.

The above summary of the present invention is not intended to represent each embodiment or every aspect of the present invention. The detailed description and Figures will describe many of the embodiments and aspects of the present invention.

BRIEF DESCRIPTION OF THE DRAWINGS

The foregoing and other advantages of the invention will become apparent upon reading the following detailed description and upon reference to the drawings.

Figure 1:
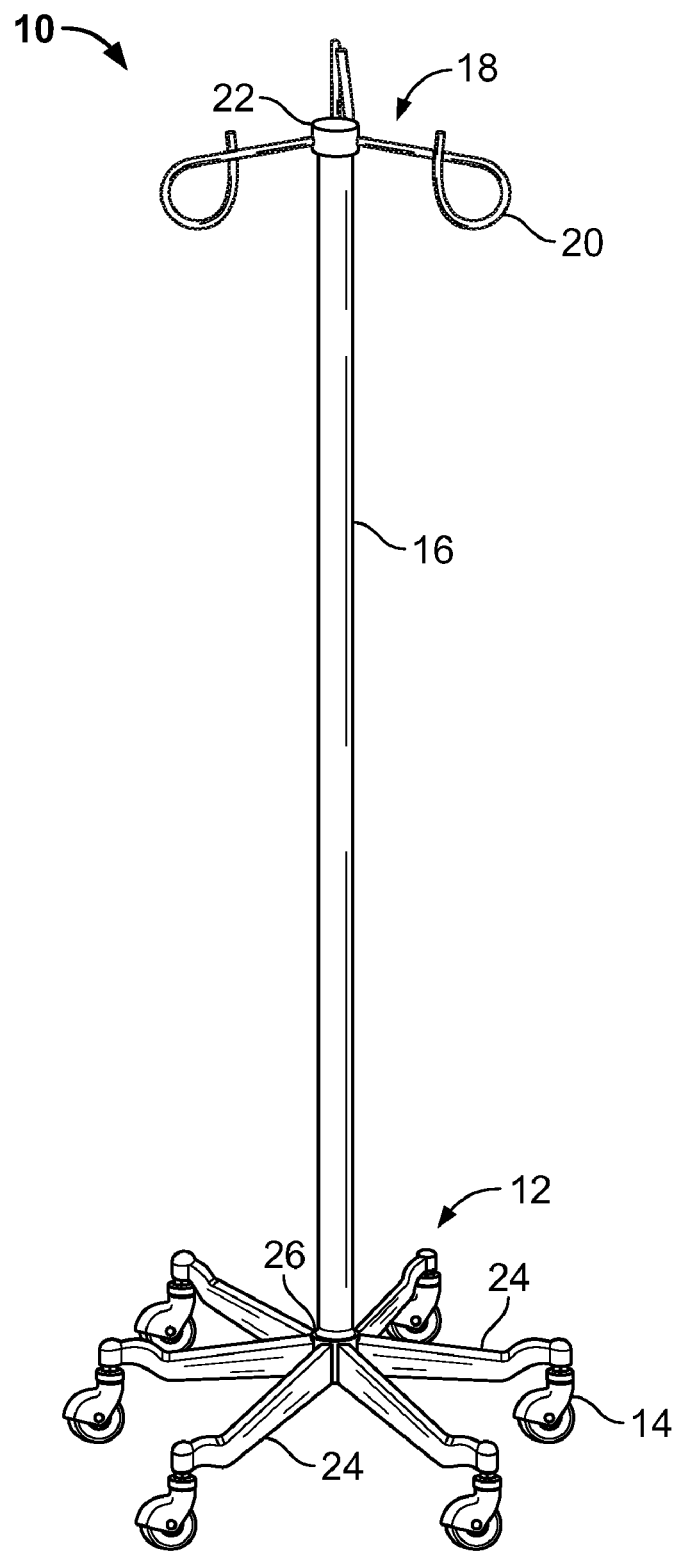
FIG. 1 is a perspective view of an intravenous stand according to one embodiment.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

As shown in FIG. 1, an intravenous (hereinafter "IV") stand 10 includes a base 12 having a plurality of casters 14, a pole 16 securely coupled to and extending generally upwardly from the base 12, and a hanger 18 configured to support one or more intravenous fluid containers (not shown) such as, for example, an IV medication bag. The hanger 18 may comprise any suitable means for supporting intravenous fluid containers, including, e.g., one or more hooks 20 radially extending from a cap 22 secured to the top end of the pole 16 as shown in FIG. 1. The pole 16 may be configured to support additional intravenous equipment (not shown) such as, for example, pumps or monitors.

The base 12 is configured to have a shape, size, and weight that sufficiently stabilizes the IV stand 10 when stationary or during transport. For example, as shown in FIG. 1, the base 12 can include six equally spaced base legs 24 extending outwardly from a base hub 26. It is contemplated that any other number of legs 24 may be provided or any other suitable base 12 configuration may be utilized to stabilize the IV stand 10. The base legs 24 can be integrally formed with the base hub 26 or coupled to the base hub 26 by any suitable means such as, for example, welds, bolts, screws, steel casting, extrusion, blow molding, and/or the like.

Figure 2:
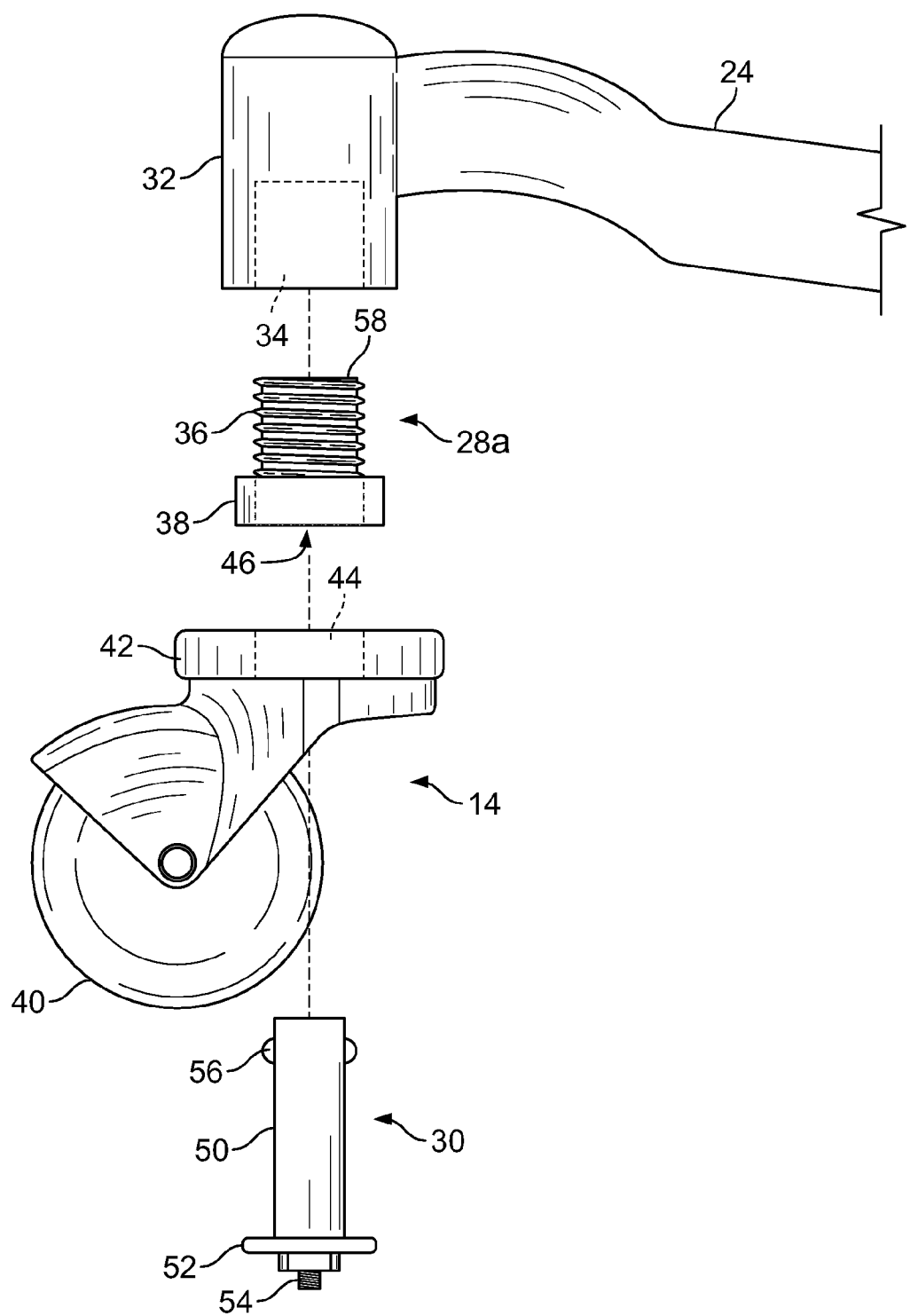
FIG. 2 is an exploded side view illustrating a caster releasably attached to a base of the intravenous stand of FIG. 1.

Referring to FIG. 2, according to one embodiment, each caster 14 is releasably coupled to a caster connector 28a (which is threaded inside a mounting head 32 of the base leg 24) via a quick-release member 30. As used herein, the term "releasably coupled" refers to a state of coupling between two components (e.g., between the quick-release member 30 and the caster connector 28a) such that one component (e.g., the quick-release member 30) may be quickly removed from or attached to the other component (e.g., the caster connector 28a) without the aid of tools, but when attached the components are secured such that simply pulling with force will not uncouple the components. Thus, the quick-release member 30 allows quick and easy replacement of a defective caster 14, without the use of tools or special expertise.

It will be appreciated by one skilled in the art that a caster 14, a caster connector 28a, and a quick-release member 30 is provided for each of the plurality of base legs 24. For simplicity, the assembly of a single caster 14, caster connector 28a, base leg 24, and quick-release member 30 will be described; however, it will be appreciated that the principles described are equally applicable to each caster 14, each caster connector 28a, each base leg 24, and each quick-release member 30 of the IV stand 10.

A mounting head 32 is located, optionally, at a distal portion of the base leg 24 relative to the base hub 26. The mounting head 32 includes a threaded bore 34 into which the caster connector 28a is coupled. The caster connector 28a is generally tubular with an exteriorly threaded portion 36 at its upper end and a flange portion 38 at its lower end. Accordingly, the threaded portion 36 of the caster connector 28a is configured to be threadedly engaged with the threaded bore 34 of the mounting head 32.

The caster 14 includes a wheel 40 and a mounting element 42. The mounting element 42 has a mounting aperture 44 therein of a diameter approximately equal to the diameter of an axial aperture 46 within the caster connector 28a. Prior to releasable coupling, the caster connector 28a is screwed into the threaded bore 34 in the base leg 24 and the mounting aperture 44 in the mounting element 42 of the caster 14 is axially aligned with the axial aperture 46 in the caster connector 28a.

The quick-release member 30 is generally a quick-release bolt having a stem 50, a flange portion 52, a push button 54, and at least one radially retractable ball 56 that is spring biased to at least partially protrude from the stem 50. The push button 54 is spring biased in the released position, causing the retractable ball(s) 56 to at least partially extend from the stem 50. When the push button 54 is depressed, the retractable balls 56 retract into the stem 50. The quick-release member 30 can be inserted through the mounting element 42 of the caster 14 and into the caster connector 28a by depressing the push button 54 and thereby causing the retractable balls 56 to retract. A further description of the quick-release member 30 is provided below in reference to FIG. 3 and FIG. 6.

The caster connector 28a and the quick-release member 30 may each have a length such that when the quick-release member 30 is fully inserted, the flange portion 52 of the quick-release member 30 is held in contact with a bottom surface of the mounting element 42. Likewise, a top surface of the mounting element 42 may be held in contact with a bottom surface of the flanged portion 38 of the caster connector 28a. It is contemplated that the length of each component may be designed to allow sufficiently tight contact such that the casters 14 are firmly supported, yet still permit quick and easy coupling/decoupling of the casters 14.

The threaded bore 34 within the mounting head 32 has a diameter and depth such that a portion of the quick-release member 30 can extend into the threaded bore 34 beyond an inner lip 58 of the caster connector to permit the retractable balls 56 to extend from the stem 50. To quickly uncouple a caster 14, a user simply depresses the push button 54 (to permit the retractable balls 56 to retract inside the stem 50) and pulls the caster 14 (along with the quick-release member 30) away from the caster connector 28a and base 12.

Figure 3:
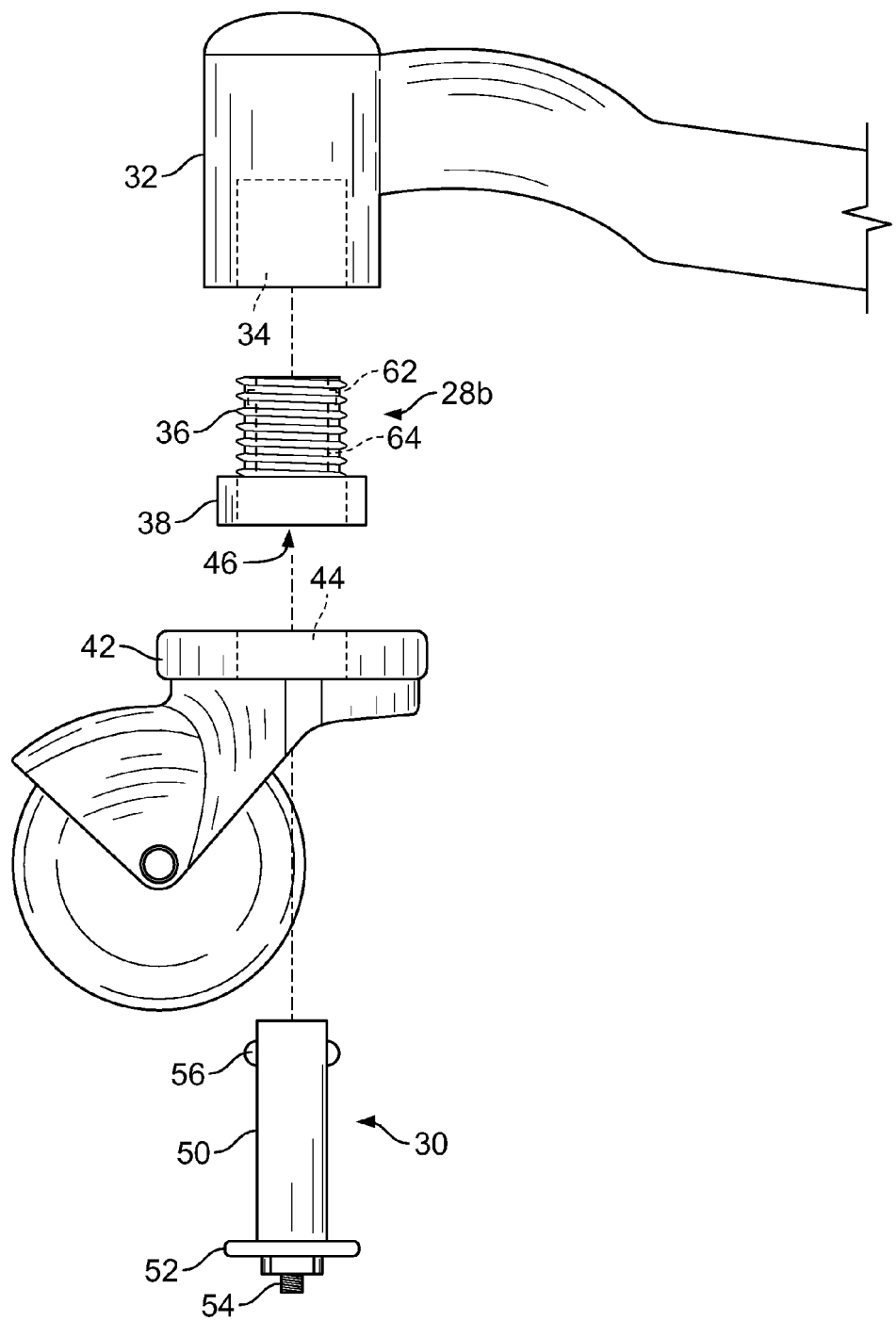
FIG. 3 is an exploded side view illustrating a caster releasably attached to a base of the intravenous stand of FIG. 1 according to an alternative embodiment.

Alternative caster connectors may be used in some alternative embodiments of the IV stand 10. For example, FIG. 3 shows an alternative caster connector 28b having grooves 62 circumferentially cut into the tubular interior surface 64 of the caster connector 28b. When the quick-release member 30 is inserted through the mounting element 42 and into the caster connector 28b, the push button 54 is released causing the retractable balls 56 to extend into the grooves 62. The grooves 62 can be of sufficient depth and width to allow the retractable balls 56 to extend into the grooves 62 with minimal clearance. The grooves 62 can be positioned in the caster connector 28b to allow the retractable balls 56 to extend into the grooves 62 when the quick-release member 30 is fully inserted into the caster connector 28b such that the flange portion 52 of the quick-release member 30 causes the top surface of the mounting element 42 to be tightly pressed against the flange portion 38 of the caster connector 28b. Accordingly, if these grooves 62 are included in the caster connector 28b, it is unnecessary for the bore 34 within the mounting head 32 to allow additional space for a portion of the quick-release member 30 to extend beyond the caster connector 28b.

Figure 4:
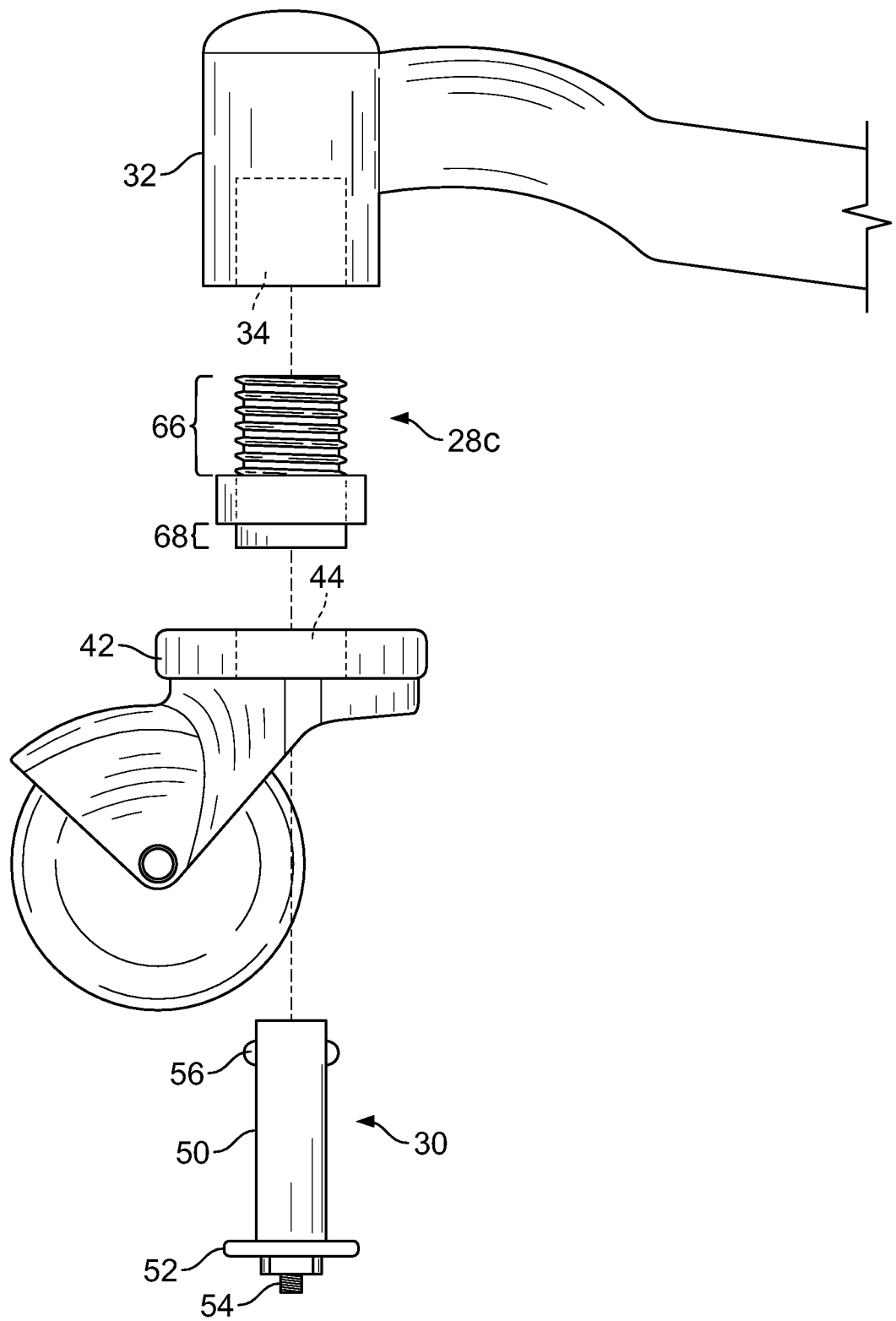
FIG. 4 is an exploded side view illustrating a caster releasably attached to a base of the intravenous stand of FIG. 1 according to another alternative embodiment.

As another example of an alternative caster connector, FIG. 4 shows a caster connector 28c having a shape and size that is configured to allow threaded engagement with the threaded bore 34 at an upper end 66 and insertion through the mounting aperture 44 at a lower end 68. The lower end 68 can have a diameter and depth such that it may be inserted within the mounting aperture 44 in the mounting element 42 with minimal clearance.

Figure 5A:
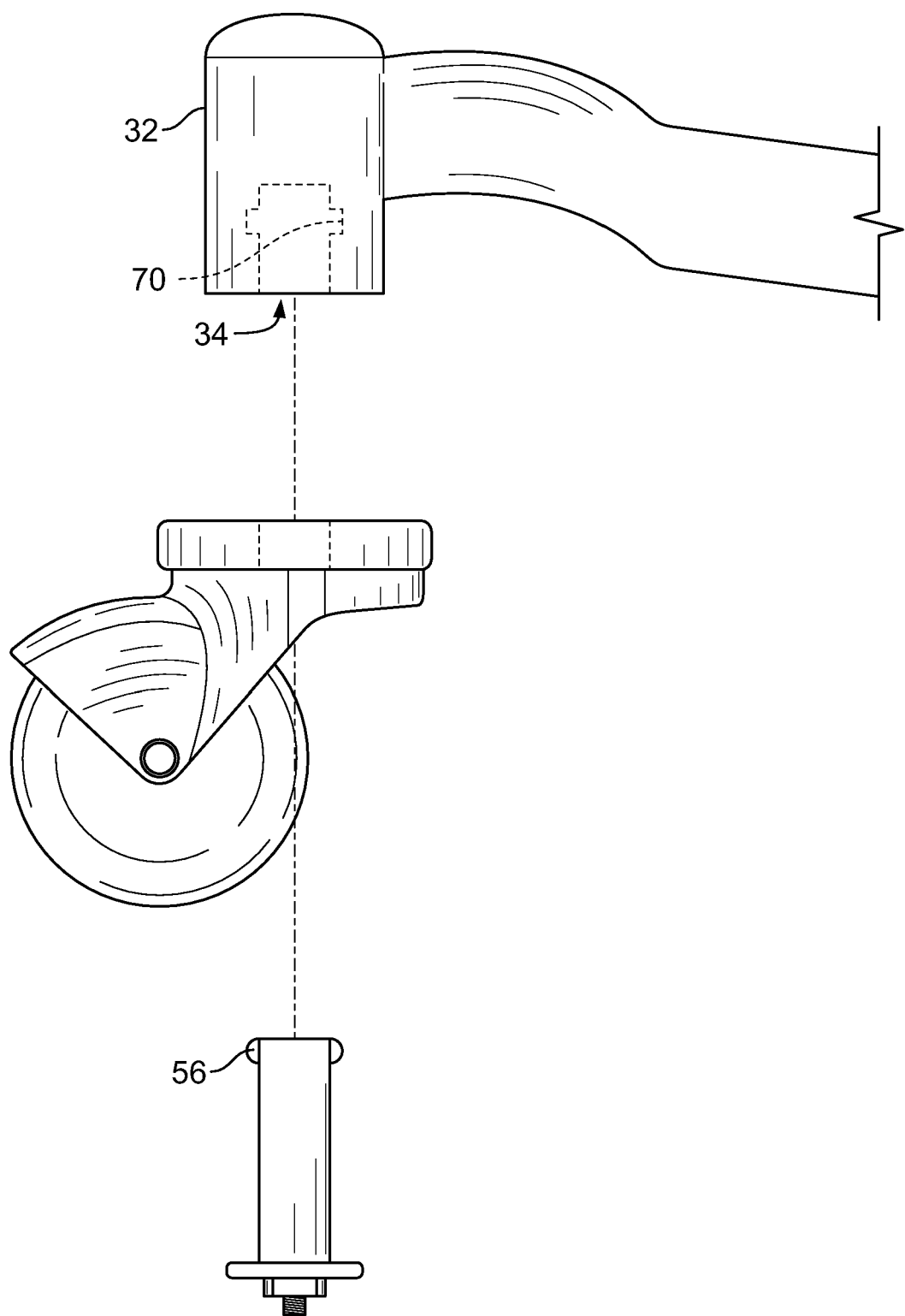
FIG. 5a is an exploded side view illustrating a caster releasably attached to a base of the intravenous stand of FIG. 1 according to yet another alternative embodiment.
Figure 5B:
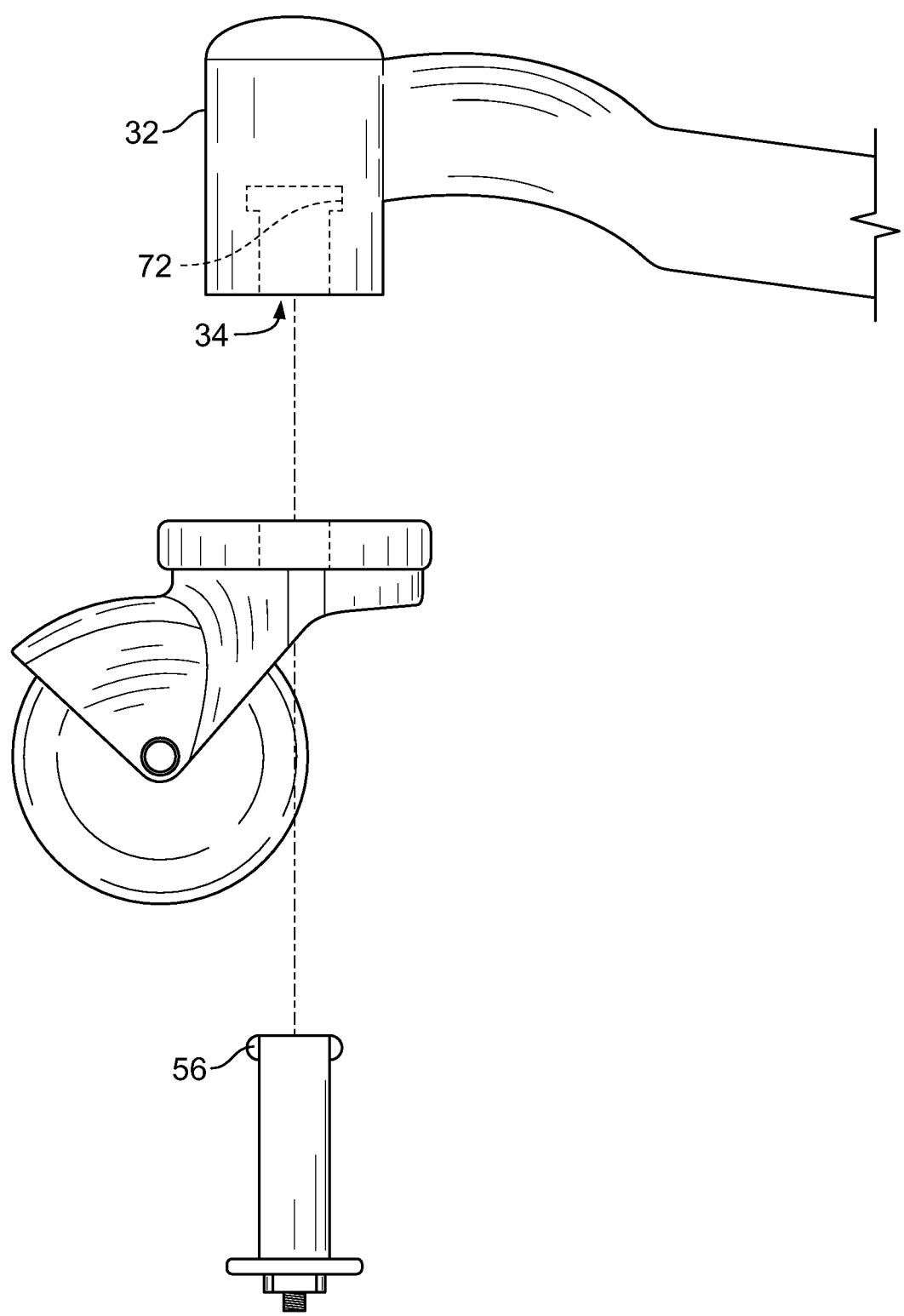
FIG. 5b is an exploded side view illustrating a caster releasably attached to a base of the intravenous stand of FIG. 1 according to still another alternative embodiment.

It is contemplated that according to further alternative embodiments, the threaded portion of the caster connector is an exteriorly smooth surface, i.e., a threadless surface. Accordingly, the caster connector may be integrally formed or attached to the base by means other than threaded engagement, e.g., welding, adhesive, steel casting, extrusion, blow molding, etc. According to still further alternative embodiments, each caster may be connected to the base without a caster connector. For example, a groove 70 (FIG. 5a) or an inner lip 72 (FIG. 5b) may be provided within the bore 34 of the mounting head 32 and configured to receive the retractable balls 56 as previously described above.

Figure 6:
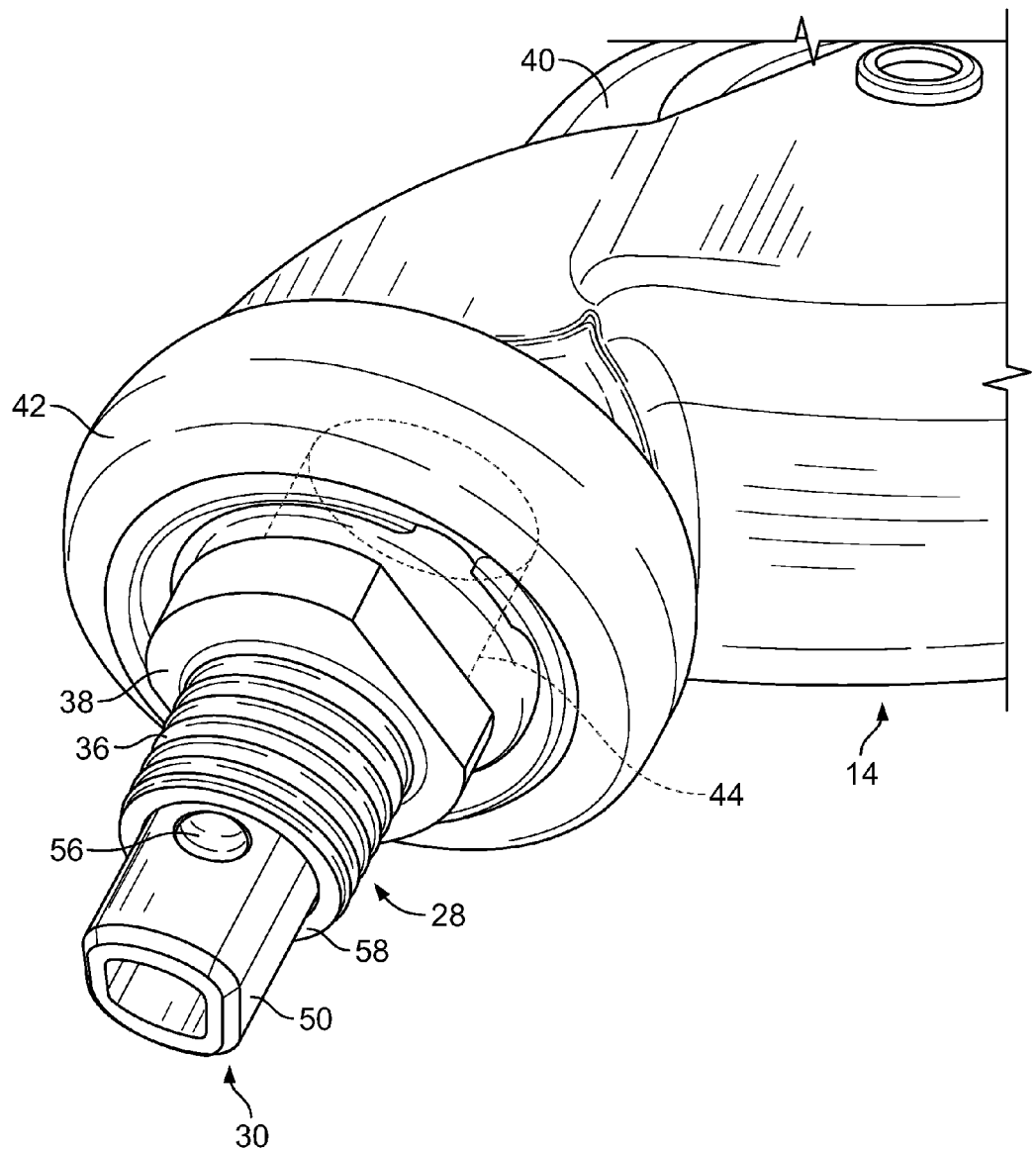
FIG. 6 is a perspective view illustrating the caster of FIG. 2 in an assembled position.

Referring to FIG. 6, the quick-release member 30 extends axially through the center of the mounting aperture 44 in the mounting element 42 of the caster 14 and into the axial aperture 46 within the caster connector 28a. The quick-release member 30 has a diameter that allows the quick-release member 30 to slide into the caster connector 28a with minimal clearance to maintain a firm coupling and minimize wobbling. The quick-release member 30 may be any suitable means for coupling a caster 14 to the base 12 such that the caster 14 can be removed from or attached to the base 12 quickly and without the aid of tools. However, the quick-release member 30 must not uncouple simply by pulling the quick-release member 30 from the caster connector 28a.

When the quick-release member 30 is fully inserted through the mounting element 42 and into the caster connector 28a, the push button 54 is released causing the retractable balls 56 to extend with minimal clearance adjacent an inner lip 58 of the caster connectors 28a. The retractable balls 56 radially extend from the stem 50 past the inner lip 58 by a sufficient distance to hold the quick-release member 30 in place.

It is contemplated that any other suitable quick-release member may be provided. For example, the quick-release member may be square, triangular or octagonal shaped instead of circular or the quick-release member may include a release lever instead of a push button. Also, in addition to and/or instead of casters, wheels (which may rotate, but may not swivel to change a direction of movement) can be included within or attached to the exterior of the base.

Figure 7:
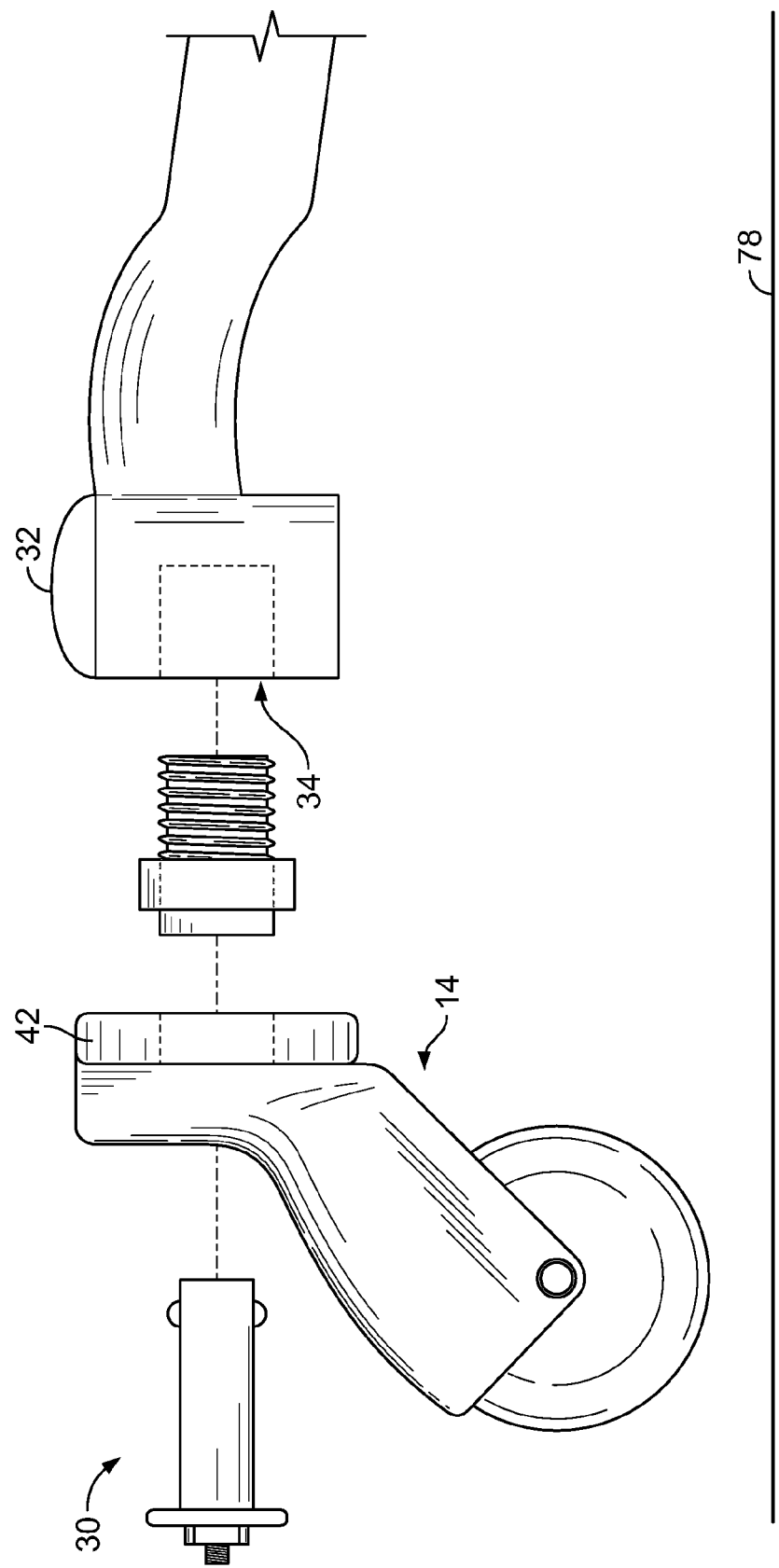
FIG. 7 is an exploded side view illustrating a caster releasably attached to a base of the intravenous stand according to another alternative embodiment.
Figure 8:
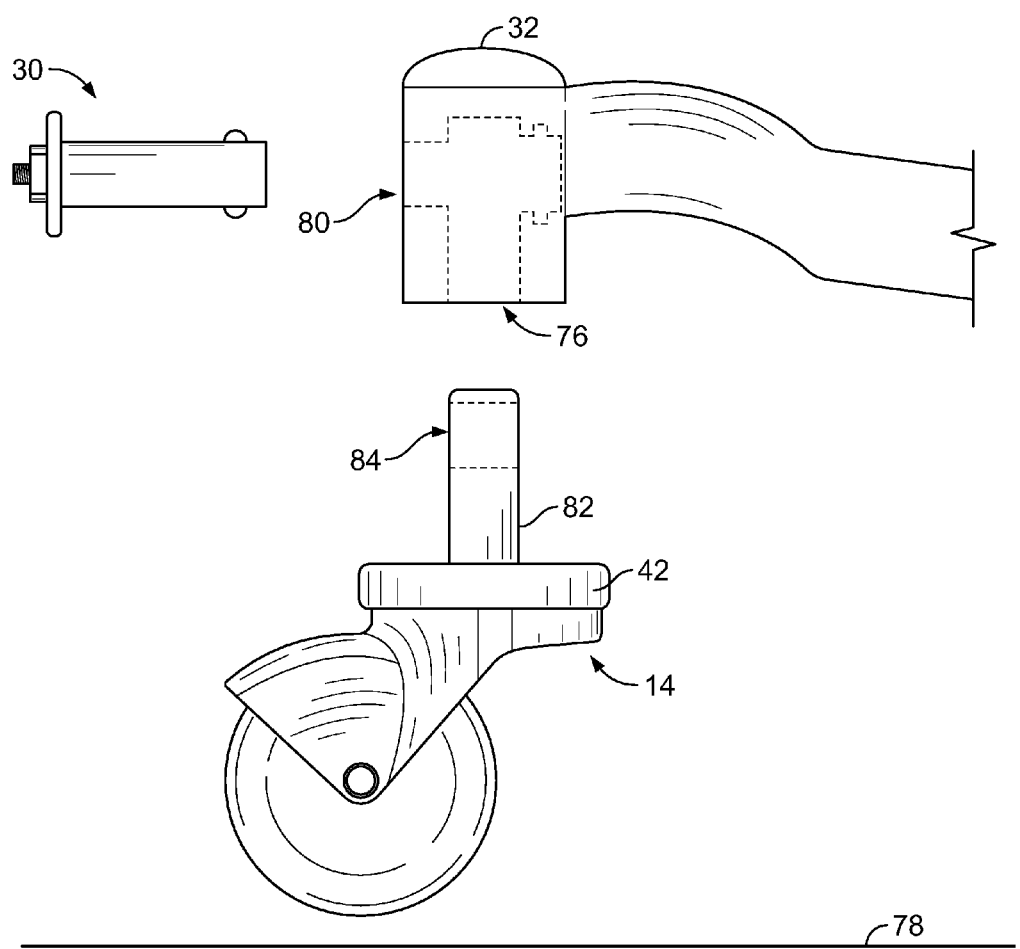
FIG. 8 is an exploded side view illustrating a caster releasably attached to a base of the intravenous stand according to yet another alternative embodiment.

It is further contemplated that the quick-release member can releasably couple a caster to the base in any other suitable configuration. For example, the bore 34 in the mounting head 32 illustrated in FIGS. 1-6 is substantially perpendicular to a floor surface 78; however, it is contemplated that the bore 34 in the mounting head 32 can be angled or parallel to the floor surface 78 as illustrated in FIG. 7. The mounting element 42 of the caster 14 can be appropriately modified to permit releasable coupling via a quick-release member 30 inserted through the mounting element 42 and the angled or parallel bore 34 of the mounting head 32. As another example, the mounting head can have two bores instead of one as illustrated in FIG. 8. The first bore 76 being substantially perpendicular to the floor surface 78 and the second bore 80 being substantially parallel to the floor surface 78. A caster 14 having a stem 82 extending from the mounting element 42 of the caster 14 can be inserted through the first bore 76 and a quick-release member 30 can be inserted through the second bore 80 to releasably couple the caster 14 to the mounting head 32. Specifically, the quick-release member 30 can be inserted through an aperture 84 in the caster stem 82 to releasably couple the caster 14 to the mounting head 32.

According to some of the embodiments described above, the IV stand may be made or assembled by providing a hanger that is configured to support one or more intravenous fluid containers, coupling a pole to the hanger at one end of the pole, coupling a base to the other end of the pole, and releasably coupling a plurality of casters to the base via a plurality of quick-release members.

Figure 9:
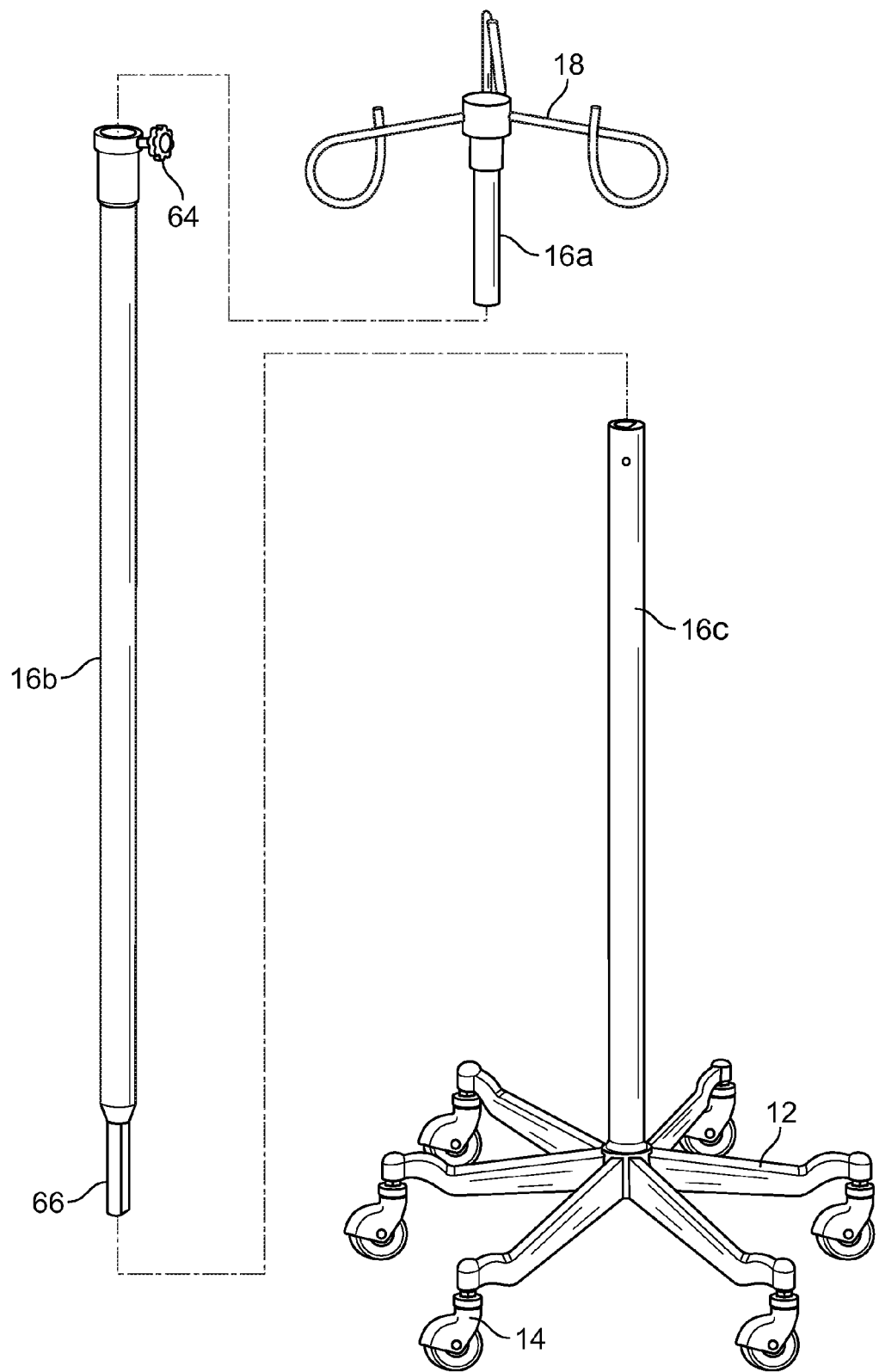
FIG. 9 is an exploded perspective view of an intravenous stand according to another embodiment.

Referring to FIG. 9, the pole 16 optionally includes an upper member 16a, an intermediate member 16b, and a lower member 16c. The top end of the upper member 16a is secured to the hanger 18. The bottom end of the upper member 16a telescopes into the intermediate member 16b and can be locked in a selected height position by a clamping device 64. Any suitable clamping device 64 can be provided including, but not limited to, a threaded locking knob mated with a hole tapped through the intermediate member 16b. According to an alternative embodiment, the height of the upper member 16a can be adjusted to suit the needs of an individual patient or the upper member 16a may be easily removed from the intermediate member 16b and inserted into a socket of a gurney or wheel chair if desired.

The intermediate member 16b is coupled to the lower member 16c via a configuration that prevents relative rotation between the intermediate and lower pole members 16b, 16c. This obviates problems often encountered where the intravenous tubing becomes entangled or wrapped around the pole. Additionally, preventing rotation of the intermediate 16b and lower 16c members can reduce wear and tear on the IV stand 10.

According to one configuration, the intermediate member 16b includes an insert 66 extending from its bottom end. The insert 66 can be integrally formed with the intermediate member 16b or can be a separate member fixedly secured within the intermediate member 16b. If the insert 66 comprises a separate member, any suitable means may be provided for fixedly securing the insert 66 to the intermediate member 16b.

Figure 10:
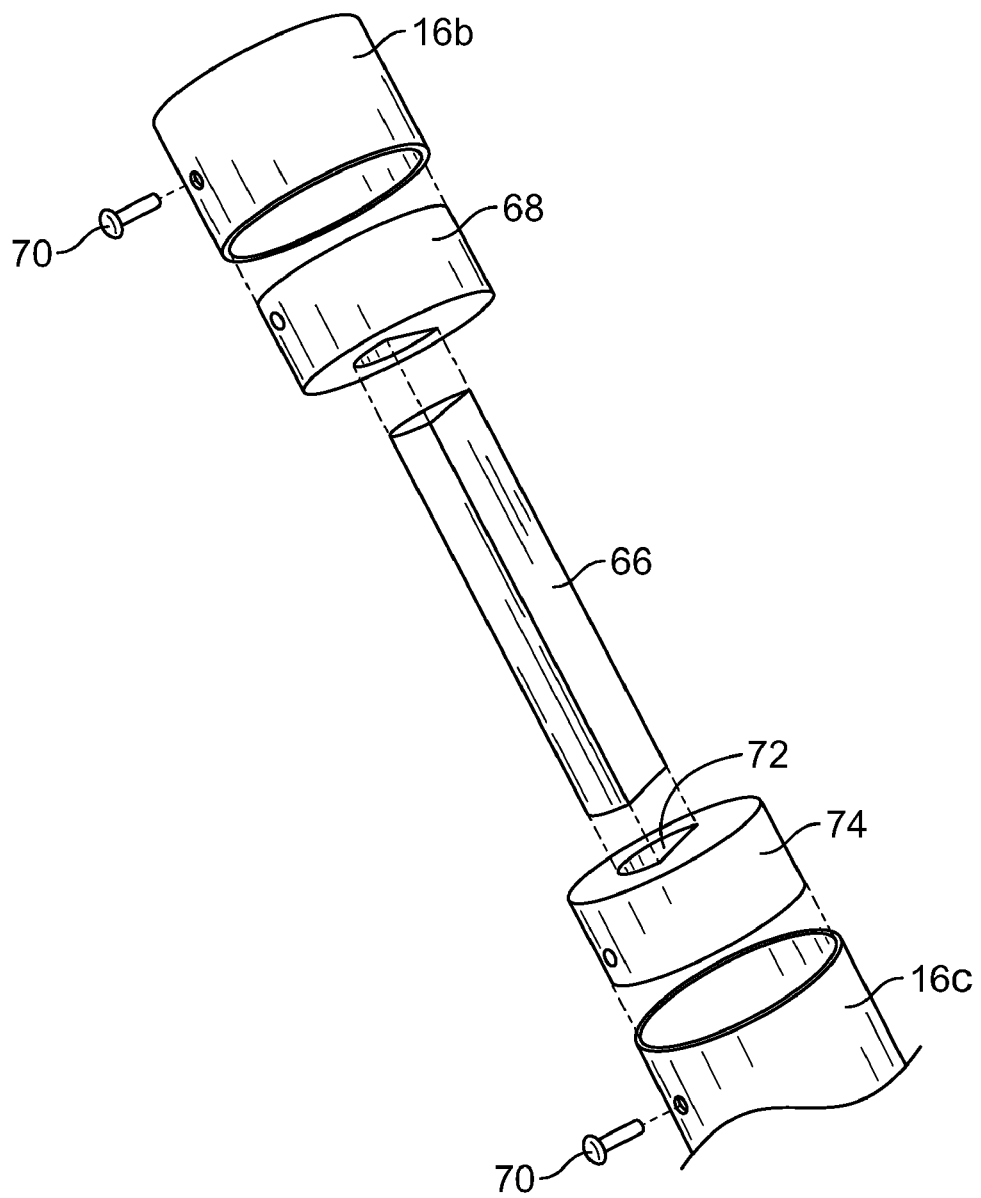
FIG. 10 is an exploded perspective view illustrating a coupling between an intermediate pole and a lower pole of the intravenous stand of FIG. 9.

For example, referring to FIG. 10, a fitting sleeve 68 can be received telescopically in the bottom end of the intermediate member 16b and fixed therein rigidly by suitable means such as, for example, a cross pin or rivet 70, which is engaged through registering apertures of the intermediate member 16b. The insert 66 can, then, be fixed centrally within the fitting sleeve 68 such that a portion of the insert 66 extends beyond the fitting sleeve 68.

The lower member 16c may be tubular or otherwise have a centrally located opening 72 at its top end. The opening 72 is sized and shaped to receive the cross section of the insert 66 such that the insert 66 may be closely slid within the opening 72 with minimal clearance. The opening 72 may be integrally formed with the top end of the lower member 16c or the opening 72 may be formed by a receiver sleeve 74 located within the top end of the lower member 16c. The receiver sleeve 74 can be fixed concentrically within the top end of the lower member 16c by suitable means such as, for example, the cross pin 70. Additionally, the insert 66 and opening 72 can each have a length and depth, respectively, to allow the bottom end of the intermediate member 16b to be flush with the top end of the lower member 16c. The insert 66 can be secured within the lower member 16c by any suitable means. For example, a locking pin (not shown) can be received through a radial aperture in the lower pole and an aligned aperture in the insert.

To prevent rotation of the intermediate member 16b relative to the lower member 16c, the insert 66 and the opening 72 have non-circular or asymmetric cross sections. For example, the insert 66 and the opening 72 can be D-shaped (as shown in FIG. 5), rectangular, hexagonal, triangular, or the like. The insert 66 and the opening 72 can be any suitable size.

It is contemplated that, according to alternative embodiments, the insert 66 may be secured to the lower member 16c and the opening 72 may instead be provided in the intermediate member 16b.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. An intravenous stand for supporting an intravenous fluid container, comprising:
   a hanger configured to support one or more intravenous fluid containers;
   a pole having a first end and a second end, the pole being coupled to the hanger at the first end;
   a base coupled to the pole at the second end;
   a plurality of casters releasably coupled to the base via a plurality of quick-release members; and
   a plurality of caster connectors having an axial aperture therein, each of the plurality of caster connectors having a surface configured to be mounted to a corresponding bore in the base and an inner lip at an upper end of the surface such that a portion of the quick-release member is extended beyond the inner lip and into the corresponding bore,
   wherein each of the plurality of casters includes a mounting element with a mounting aperture therein, each of the plurality of quick-release members being configured to releasably couple a corresponding caster to the base by insertion through the mounting aperture and the axial aperture to provide sufficient contact for supporting the plurality of casters.

2. The intravenous stand of claim 1, wherein each quick-release member includes a stem, a push button, and at least one radially retractable ball that is spring biased to at least partially protrude from the stem.

3. The intravenous stand of claim 2, wherein the push button is coupled to the at least one radially retractable ball such that the push button causes the at least one radially retractable ball to retract at least partially within the stem when the push button is depressed.

4. The intravenous stand of claim 1 wherein, each of the plurality of caster connectors has a threaded exterior surface configured to be mounted in a corresponding threaded bore in the base.

5. The intravenous stand of claim 2, wherein upon insertion of the quick-release member, the at least one retractable ball extends away from the stem and adjacent to the inner lip of the caster connector.

6. The intravenous stand of claim 4, wherein the base includes a base hub and a plurality of base legs extending outwardly from the base hub, the base being coupled to the second end of the pole at the base hub, and the plurality of threaded bores being located at a distal portion of the plurality of base legs relative to the base hub.

7. The intravenous stand of claim 1, wherein the pole comprises at least a first member and a second member, the first member being coupled to the second member via a D-shaped insert to prevent rotational movement between the first member and the second member.

8. The intravenous stand of claim 7, wherein the D-shaped insert is integral with one of the first member or the second member.

9. The intravenous stand of claim 7, wherein the D-shaped insert extends from the first member and the second member has an opening configured to receive the D-shaped insert.

* * * * *

UNITED STATES PATENT AND TRADEMARK OFFICE
CERTIFICATE OF CORRECTION

| | | |
|---|---|---|
| PATENT NO. | : 8,313,066 B2 | Page 1 of 1 |
| APPLICATION NO. | : 12/146147 | |
| DATED | : November 20, 2012 | |
| INVENTOR(S) | : Hampton et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 917 days.

Signed and Sealed this
Eleventh Day of November, 2014

Michelle K. Lee
*Deputy Director of the United States Patent and Trademark Office*